United States Patent

Solecki

(10) Patent No.: US 9,427,298 B2
(45) Date of Patent: Aug. 30, 2016

(54) TEXTILE IMPLANT, IN PARTICULAR FOR REPAIRING HERNIAS

(75) Inventor: Gilles Solecki, Lannoy (FR)

(73) Assignee: Bard Shannon Limited, Humacao, PR (US)

( * ) Notice: Subject to any disclaimer, the term of this patent is extended or adjusted under 35 U.S.C. 154(b) by 811 days.

(21) Appl. No.: 12/675,339

(22) PCT Filed: Aug. 29, 2008

(86) PCT No.: PCT/FR2008/051545
§ 371 (c)(1),
(2), (4) Date: Jun. 29, 2010

(87) PCT Pub. No.: WO2009/030867
PCT Pub. Date: Mar. 12, 2009

(65) Prior Publication Data
US 2010/0305589 A1    Dec. 2, 2010

(30) Foreign Application Priority Data
Sep. 7, 2007 (FR) ...................... 07 57427

(51) Int. Cl.
*A61F 2/00* (2006.01)
*A61L 24/00* (2006.01)
*A61L 24/06* (2006.01)
*A61L 31/10* (2006.01)

(52) U.S. Cl.
CPC .......... *A61F 2/0063* (2013.01); *A61L 24/0042* (2013.01); *A61L 24/06* (2013.01); *A61L 31/10* (2013.01); *A61F 2210/0004* (2013.01)

(58) Field of Classification Search
CPC .. A61F 2/0063; A61F 2/0045; A61F 2/0077; A61F 2210/00; A61F 2210/0004
USPC ............................... 606/151, 200; 623/23.72
See application file for complete search history.

(56) References Cited

U.S. PATENT DOCUMENTS

| | | | |
|---|---|---|---|
| 3,759,264 A * | 9/1973 | Coover et al. ................. | 606/214 |
| 5,405,366 A * | 4/1995 | Fox et al. ........................ | 607/50 |
| 6,551,704 B2 * | 4/2003 | Himmelsbach et al. ..... | 428/343 |
| 2002/0049503 A1 * | 4/2002 | Milbocker ................. | 623/23.72 |
| 2003/0149387 A1 * | 8/2003 | Barakat et al. ................. | 602/45 |
| 2004/0096422 A1 * | 5/2004 | Schwartz et al. .......... | 424/78.37 |
| 2005/0080431 A1 * | 4/2005 | Levine et al. ................. | 606/108 |
| 2006/0116696 A1 | 6/2006 | Odermatt et al. | |
| 2007/0088391 A1 * | 4/2007 | McAlexander et al. ...... | 606/232 |
| 2007/0129736 A1 * | 6/2007 | Solecki ......................... | 606/151 |
| 2008/0091207 A1 * | 4/2008 | Truckai et al. ................. | 606/79 |
| 2009/0149875 A1 * | 6/2009 | Abele et al. .................. | 606/151 |
| 2009/0204129 A1 * | 8/2009 | Fronio ......................... | 606/151 |

FOREIGN PATENT DOCUMENTS

| | | | | |
|---|---|---|---|---|
| EP | | 588756 A2 * | 3/1994 | ............... A61F 2/50 |
| JP | | 2006-509530 | 3/2006 | |

(Continued)

*Primary Examiner* — Dianne Dornbusch
(74) *Attorney, Agent, or Firm* — Wolf, Greenfield & Sacks, P.C.

(57) ABSTRACT

A textile implant, in particular for repairing hernias, the implant including a textile piece having a first face completely or partially covered in a bio-adhesive composition that is hydrosoluble and absorbable and that includes at least one bioadhesive polymer that is hydrosoluble and absorbable, with the adhesive function thereof being activatable in a moist or wet medium. The bio-adhesive composition includes less than 4% by weight of plasticizer.

12 Claims, 2 Drawing Sheets

(56) References Cited

FOREIGN PATENT DOCUMENTS

| WO | WO 97/29715 A1 | 8/1997 |
| WO | WO 97/35533 A1 | 10/1997 |
| WO | WO 00/10618 A1 | 3/2000 |
| WO | WO 2004-012678 A2 | 2/2004 |
| WO | WO 2005/058383 A1 | 6/2005 |
| WO | WO 2007101630 A1 * | 9/2007 |

* cited by examiner

TEXTILE IMPLANT, IN PARTICULAR FOR REPAIRING HERNIAS

This is a 371 national phase application of PCT/FR2008/051545 filed 29 Aug. 2008, claiming priority to French Patent Application No. 0757427 filed 7 Sep. 2007, the contents of which are incorporated herein by reference.

FIELD OF THE INVENTION

The present invention lies in the technical field of textile implants, in particular for repairing hernias, such as an implant comprising a textile piece having a first face that is totally or partially covered in a bio-adhesive composition that is hydrosoluble and absorbable, and that includes at least one bio-adhesive polymer that is hydrosoluble and absorbable.

BACKGROUND OF THE INVENTION

Usually, a textile piece for parietal repair is fastened to the anatomical zone for reinforcement by clips in order to guarantee durable fastening to human tissue, in particular given the mechanical stresses exerted by the abdominal muscles, internal organs, and other organs that might move the textile piece away from the position in which the practitioner implanted it.

Such clips are traumatizing in that postoperative pain is often observed, particularly when a nerve ending is pinched. In addition, suturing by means of clips is an operation that is lengthy and tedious.

To combat those drawbacks, surgical adhesives have been developed that are suitable for causing the textile piece to adhere to human tissue, where such adhesives are glues based on fibrin or on cyanoacrylate.

Fibrin adhesives are biological tissue adhesives derived from human plasma. Those adhesives contain the components required for the last step of coagulation and they are commonly used during surgery to prevent bleeding and to encourage the healing of wounds.

Fibrin adhesives are not ready for use since the formulation needs to be prepared in theater in order to avoid any risk of contamination. Such preparation is also complex and lengthy.

Fibrin adhesives have poor adhesive power in general, and particularly when compared with adhesives based on cyanoacrylate.

Cyanoacrylate adhesives have high adhesive power on human tissue but they give rise to necrosis thereof, or they may burn them by an exothermic reaction. In addition, such cyanoacrylate adhesives harden very quickly, thereby preventing the textile piece being repositioned by the practitioner over the zone for treatment. Finally, the biocompatibility of those adhesives has not been demonstrated. The exothermic hardening reaction that takes place in contact with human tissue gives off toxic substances.

Document FR 2 863 502 in the name of the Applicant describes a surgical implant comprising a textile and a biocompatible polymer, the polymer being hydrosoluble and suitable for causing the implant to adhere to human tissue under the combined action of a pressure force and water molecules. Amongst the polymers mentioned, there are in particular polyvinylpirrolidone (PVP) and carboxymethylcellulose (CMC), having adhesive properties that may optionally be adjusted by adding polyethylene glycol (PEG), and more particularly in a ratio of 64% by weight PVP and 36% by weight PEG.

Unfortunately, the textile implant described in FR 2 863 502 does not is give complete satisfaction. The Applicant has observed that in theater, when said textile implant is being put into place on human tissue, the adhesive responds to any contact as soon as its package has been opened, and thus even before it has been activated by the moist medium of the tissues. This gives rise to a significant loss of adhesive onto the practitioner's gloves and inside the package, and consequently to results that are degraded in terms both of durable fastening of the implant on tissue and of ease of repositioning. In practice, the quantity of adhesive that remains on the implant can be insufficient. Furthermore, when the textile implant is to be inserted by means of a trocar, with the implant being rolled up, the bio-adhesive composition is sticky even though it has not been activated by the moist medium of the tissues, so a fraction of the adhesive remains on both faces of the textile implant, which then runs the risk of adhering to the wall opposite from the zone to be reinforced.

Furthermore, it has been observed that the adhesive runs directly inside the packaging sachet as a result of the step of sterilizing the implant, in particular using ethylene oxide, during which step the temperature rises. Apart from the unattractive appearance of such streaking, it also gives rise to a lack of confidence with practitioners.

Following tests on animals, it has been found that a few days after implantation, the textile implant tends to collapse and then cease to be effective. Furthermore, since the adhesive power is not sufficient for fibrosis to have the time to develop and fasten the textile implant definitively, there is a tendency for the implant to move away from the position in which it was implanted by the practitioner.

SUMMARY OF THE INVENTION

The present invention provides an improved textile implant, in particular for repairing hernias, that solves the above-mentioned problems, and that in known manner comprises a textile piece having a first face completely or partially covered in a bio-adhesive composition that is hydrosoluble and absorbable and that comprises at least one bio-adhesive polymer that is hydrosoluble and absorbable, with the adhesive function thereof being activatable in a moist or wet medium. In characteristic manner, said bio-adhesive composition includes less than 4% by weight of plasticizer.

The term "plasticizer" is used to mean any substance, other than water molecules, suitable in particular for reducing the glass transition temperature (Tg) of said bio-adhesive polymer. During the steps of fabricating, sterilizing, and storing the textile implant, it being understood that molecules of water can pass through the packaging sachet, water molecules can be present in the bio-adhesive composition and can act as plasticizers.

The Applicant has observed, contrary to the recommendations of the state of the art, and as a result of a large amount of laboratory testing performed on pigs and carried out in application of Good Laboratory Practice (GLP) standards, that by selecting the quantity of plasticizer to be less than 4% of the bio-adhesive composition, it is possible to achieve a sufficient reduction in the Tg of the bio-adhesive polymer without an increase in ambient temperature, e.g. up to about 60° C. for sterilization using ethylene oxide, reaching the melting temperature of said bio-adhesive polymer, and thus avoiding the bio-adhesive composition running in the packaging sachet of the textile implant. In addition, the bio-adhesive composition does not stick to the practitioner's gloves until it has been actually activated by a moist or wet medium, and that makes handling by the practitioner easier. The bio-adhesive composition is sufficiently rigid to ensure the textile implant has good shape memory, thereby making it easier to deploy it on leaving the trocar so that it extends over the human tissue and matches closely to the zone for reinforcement.

Advantageously, the bio-adhesive composition is absorbable, which means that it dissolves progressively in the moist or wet medium of the human tissue containing a sufficient quantity of water molecules, and is then eliminated naturally by the organism. Thus, the bio-adhesive composition performs its function as a repositionable adhesive once it has been activated by the moist or wet medium on the tissue, and it holds the textile piece on said tissue in the position in which the practitioner places it without migrating, and it does so for a sufficiently long period of time to allow fibrosis and conjunctive tissue to develop so as to fasten the textile piece definitively. The textile piece then suffices on its own to act as a mechanical reinforcing agent. There is no need to make use of clips. Furthermore, since the adhesive used is eliminated by the organism, the quantity of agents foreign to the organism is reduced, thereby limiting any risk of complications and improving the tolerance of the organism with respect to said textile implant.

The textile implant of the present invention may be used in particular for repairing direct (inguinal), femoral, and umbilical hernias.

Preferably, the textile piece is a knit, of the warp or rachel type, based on monofilaments with a diameter lying in the range [0.0 millimeters (mm), 0.3 mm] selected from amongst the following polymers: polypropylene, polyamide, or polyester. Preferably, the textile piece is perforated, with apertures of millimeter order in order to encourage the attachment of conjunctive tissue that develops as a result of fibrosis on the mesh defining the apertures of said textile piece.

Preferably, the bio-adhesive composition comprises a single bio-adhesive, hydrosoluble, and absorbable polymer.

In a variant embodiment, said bio-adhesive composition includes less than 2% by weight of plasticizer, preferably selected from polyalcohols, in particular polyethylene glycol (PEG).

The Applicant has observed that a quantity of less than 2% of plasticizer achieves results that are satisfactory and enables the quantity of foreign agent in the organism to be further reduced. In addition, the Tg of the bio-adhesive polymer is lowered to a lesser extent, so the bio-adhesive composition has a smaller risk of running and becoming sticky without being activated. Polyalcohols are preferred as the plasticizer, in particular PEG, and they also act as an agent for solubilizing the bio-adhesive polymer during preparation of the bio-adhesive composition.

In a variant embodiment, the or each plasticizer has a weight average molecular mass Mw lying in the range 100 grams per mole (g/mol) to 700 g/mol.

In a variant embodiment, the or each bio-adhesive polymer is selected from the following polymers: carboxymethylcellulose (CMC); polyvinylpyrrolidone (PVP); polyacrylics; and preferably polyvinylpyrrolidone (PVP).

In a variant embodiment, the or each bio-adhesive polymer has a weight average molecular mass Mw lying in the range 44,000 g/mol to $2.10^6$ g/mol, in particular polyvinylpyrrolidone (PVP).

The Applicant has observed that if the weight average molecular mass of the bio-adhesive polymer is too low, then the bio-adhesive composition dissolves completely on first contact with human tissue. The practitioner is then prevented from repositioning the textile implant on the tissue since there is practically no adhesive left. Since its adhesive power is reduced, the textile implant migrates and does not remain properly in place on the zone for reinforcing.

A weight average molecular mass lying in the range 44,000 g/mol to $2.10^6$ g/mol enables the above-mentioned problems to be mitigated. Its Mw preferably lies in the range $[1.10^6, 2.10^6]$ g/mol, thereby giving results that are improved in terms of adhesive power for repositioning of the textile implant by the practitioner and in terms of keeping the textile piece in place long enough to allow fibrosis to develop. When repairing hernias, the Applicant has found that the higher the weight average molecular mass of the bio-adhesive polymer, the greater the adhesive power of said bio-adhesive composition.

In a variant embodiment, the bio-adhesive composition is placed on the first face of said textile piece in patterns that are spaced apart from one another by at least 1 mm, and preferably by at least 1.5 mm.

Given that the weight average molecular mass is high and that the quantity of plasticizer must be less than 4% by weight of the bio-adhesive composition, so as to avoid the textile implant becoming sticky without being activated and/or so as to avoid it running in the packaging sachet, the bio-adhesive composition is rather rigid (in particular when the quantity of plasticizer is less than 2% and even more so when it is about 1%), and it tends to crack when the textile implant is rolled up for placing in a trocar, should the practitioner apply too small a radius of curvature thereto, e.g. greater than 30%. By spacing apart the patterns of the bio-adhesive composition by at least 1 mm, and preferably by at least 1.5 mm, the Applicant has found that it is possible to roll the textile implant up so that it can be inserted into a trocar with a diameter of 10 mm or 12 mm, without the dry bio-adhesive composition cracking.

In a variant embodiment, said patterns are parallel strips, preferably having a width of about 4 mm and spaced apart by about 2 mm.

The textile implant is thus advantageously rolled up with the parallel strips being folded one against another. The fold zones between pairs of strips preferably correspond to the zones that are free of bio-adhesive composition between said strips, particularly when these zones have a width of about 2 mm.

In a variant embodiment, said patterns are so-called "chiral" patterns, i.e. they are not superposable on their own mirror images, and they are preferably S-shaped, having a width of about 5 mm to 8 mm, a height of about 20 mm, and being spaced apart by about 1.5 mm.

Depending on the nature of the bio-adhesive polymer and on the plasticizer used, in particular when PVP is used with PEG, the bio-adhesive is composition is usually transparent. The Applicant has found that once the bio-adhesive composition has been applied on a perforated textile piece, e.g. a knit of monofilaments of polyproplene (PP), the practitioner in theater cannot easily distinguish between the first face carrying the activatable adhesive function and the second face. Advantageously, the arrangement whereby the bio-adhesive composition is coated on the first face in chiral patterns mitigates the above problem by enabling the practitioner to identify the first face of the textile implant easily and quickly without wetting said first face prior to implantation.

In a variant embodiment, the weight per unit area of the textile piece lies in the range [15, 200] grams per square meter (g/m²), and preferably in the range [30, 100] g/m².

Preferably, the textile piece is a knit of the warp or rachel type comprising monofilaments of polypropylene and having apertures of millimeter order, thereby facilitating the attachment of conjunctive tissue to said textile piece as developed as a result of fibrosis.

In a second aspect, the present invention provides a textile implant, in particular for intra-abdominal extra-peritoneal repair of hernias, the implant being in accordance with the variant embodiments described above, and including in characteristic manner a bio-adhesive composition of weight per unit area of that is greater than or equal to three times the weight per unit area of the textile piece.

Although in the design of an implant, the purpose is to minimize the quantity of foreign substances in the organism, the Applicant has found that the quantity of bio-adhesive composition needed to prevent the textile implant from migrating once it has been implanted needs to be at least three times greater than the mass per unit area of the textile piece when the textile implant is placed in an intra-abdominal extra-peritoneal position. A non-exhaustive explanation is that since the textile implant is placed against the muscle wall, it is subjected to high levels of mechanical stress that might move the textile implant away from its initial implantation position, even though the peritoneum protects the textile implant from the internal organs.

The textile implant needs in particular to comply with ISO standard 10993 evaluating biocompatibility and subchronic cytotoxicity and sensitization tests. These evaluations make it possible to ensure that the organism is perfectly capable of eliminating the bio-adhesive polymer and the plasticizer and that it will tolerate the textile piece. Specifically, a large quantity of bio-adhesive composition has been tested and shown to be well tolerated and absorbed by animals after about 28 days.

In a variant embodiment, the weight per unit area of said bio-adhesive composition lies in the range [45, 600] $g/m^2$, and preferably in the range [90, 300] $g/m^2$.

The weight per unit area of the textile piece then lies in the range [15, 200] $g/m^2$, and preferably in the range [30, 100] $g/m^2$.

In a third aspect, the present invention provides a textile implant, in particular for intra-abdominal intra-peritoneal repair of hernias, in accordance with any of the above-described variant embodiments, and in which, in characteristic manner:
- the second face of the textile piece is completely or partially covered in a polymer material having a coefficient of friction of less than 0.1; and
- the weight per unit area of said bio-adhesive composition is at least equal to or greater than one-third of the weight per unit area of the textile piece.

Since the textile implant is preferably located in an intra-abdominal intra-peritoneal position, it lies between the peritoneum and the internal organs. Since said second face preferably faces the internal organs, said polymer material with a low coefficient of friction prevents them from adhering to the second face and thus to the textile implant. The first face having an activatable adhesive function is for applying to the zone that needs reinforcing.

Unlike intra-abdominal extra-peritoneal implantation, the Applicant has found that a quantity of bio-adhesive composition that is equal to or a little greater than one-third of the weight per unit area of the textile piece suffices. A non-exhaustive explanation is that the internal organs do not exert as much friction as the person skilled in the art might have thought, but on the contrary exert pressure against the second face, thereby encouraging the textile implant to remain against the peritoneum. Furthermore, the peritoneum would appear to be a region that is subjected to a lower level of mechanical stress than the abdominal wall.

The polymer material with a low coefficient of friction may be a fluorinated polymer or a polymer based on dimethylsiloxane (silicone).

In a variant embodiment, said second face is covered in a fluorinated polymer material, preferably in expanded polytetrafluoroethylene (ePTFE), in particular in the form of a film.

In a variant embodiment, said weight per unit area of the bio-adhesive composition lies in the range [5, 70] $g/m^2$, and preferably in the range [10, 40] $g/m^2$.

The weight per unit area of the textile piece then lies in the range [5, 200] $g/m^2$, and preferably in the range [30, 100] $g/m^2$.

BRIEF DESCRIPTION OF THE DRAWINGS

The present invention can be better understood on reading the following description of embodiments given by way of non-limiting example and shown in the accompanying figures, in which.

DETAILED DESCRIPTION

Figure 1:
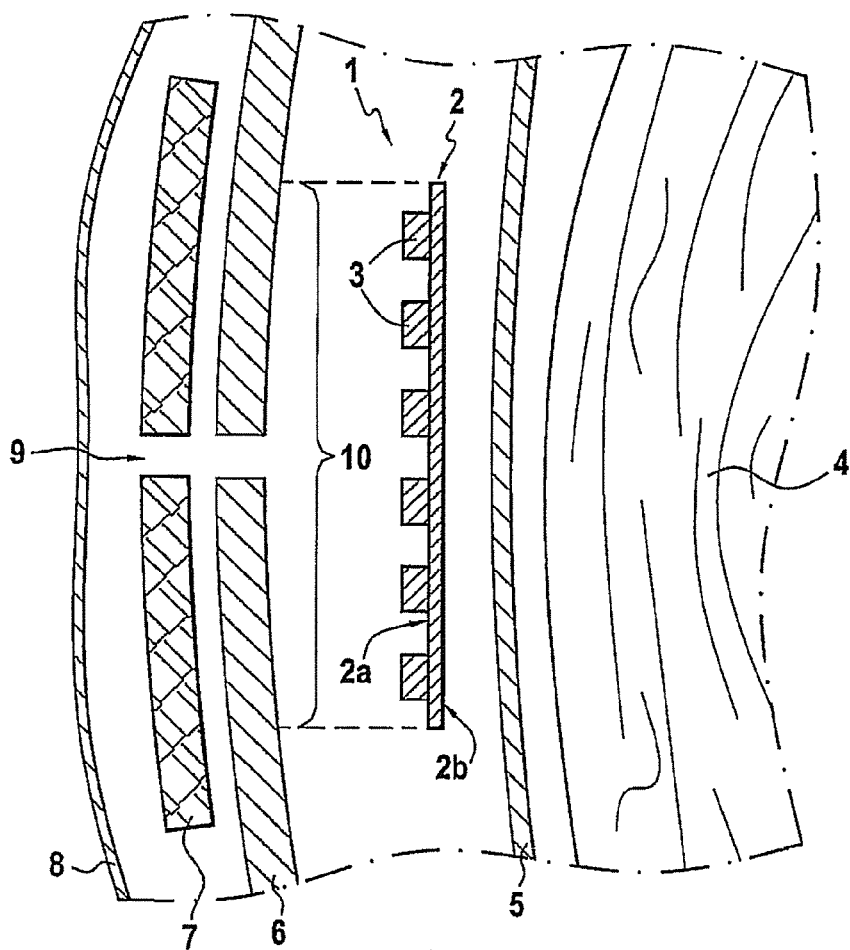
FIG. 1 is a diagrammatic cross-section view of a first example of a textile implant of the present invention shown in the organism for intra-abdominal extra-peritoneal hernia repair.
Figure 2:
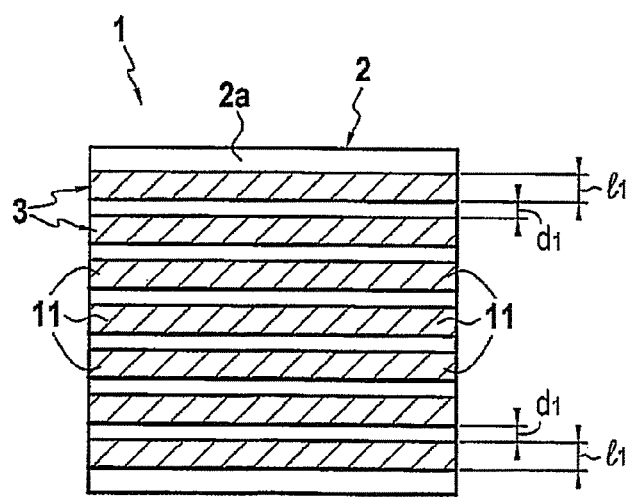
FIG. 2 is a diagrammatic view of a first variant of the first face of the textile implant shown in FIG. 1.

The textile implant 1 shown in FIGS. 1 and 2 comprises a textile piece 2 having a first face 2a and a second face 2b. The first face 2a is covered in part in a bio-adhesive composition 3 presenting an adhesive function that is activatable on coming into contact with the moist medium of tissues. The textile implant 1 is implanted in an intra-abdominal extra-peritoneal position, i.e. it is placed between the internal organs 4 and the peritoneum 5 on one side and the abdominal wall 6, a layer of adipose tissue 7, and the skin 8 on the other side.

In FIG. 1, the first face 2a of the textile implant 1 is placed facing the hernia orifice or eventration 9, closing the layer of adipose tissue 7 and the peritoneum 6, after the hernia has been dissected and pushed back (not shown). The bio-adhesive composition 3 is hydrosoluble and absorbable and preferably comprises a single bio-adhesive polymer that is hydrosoluble and absorbable with an adhesive function that is activatable on contact with the moist or wet medium of the tissue. In this particular example, the bio-adhesive polymer is polyvinylpirrolidone (PVP), preferably as sold under the trademark Kollidon 90F® by BASF and having a weight average molecular mass Mw lying in the range $1.0 \times 10^6$ g/mol to $1.5 \times 10^6$ g/mol.

The bio-adhesive composition comprises less than 2% by weight of plasticizer, preferably about 1% by weight of a polyalcohol, preferably polyethylene glycol (PEG). The preferred PEG has a weight average molecular mass lying in the range 100 g/mol to 700 g/mol. The textile piece 2 is preferably a knit, of the warp or rachel type, based on monofilaments of polypropylene of diameter lying in the range [0.01 mm, 0.3 mm], and presenting openings or apertures of millimeter order, preferably of the order of 2 mm×3 mm or 3 mm×3 mm. These openings facilitate final fastening of the textile piece 2 by conjunctive tissue developing therethrough. The textile piece 2 has a weight per unit area lying in the range [15, 200] g/m$^2$, and preferably in the range [30, 100] g/m$^2$.

The weight per unit area of the bio-adhesive composition 3 lies in the range [45, 600] g/m$^2$, and preferably in the range [90, 300] g/m$^2$. In one particular example, the textile piece 2 has a weight per unit area of about 30 g/m$^2$ and the weight per unit area of the bio-adhesive composition lies in the range 115 g/m$^2$ to 210 g/m$^2$, and is preferably about 120 g/m$^2$. The weight per unit area of the bio-adhesive composition 3 is at least three times greater than the weight per unit area of the textile piece 2, and in this particular example is about four times the weight per unit area of the textile piece 2.

On the first face 2a, the bio-adhesive composition 3 is placed with patterns 11 that are placed apart from one another by a distance d1 of at least 1 mm, and in this particular example d1 is 2 mm. The patterns 11 are parallel strips having a width l1 that is preferably 4 mm. The patterns 11 advantageously enable the textile implant 1 to be rolled up easily in the direction extending transversely to the longitudinal direction of said strip, without the bio-adhesive composition 3 cracking. Since the adhesive power of the bio-adhesive composition is strong, the weight average molecular mass of the selected bio-adhesive polymer is high, and the bio-adhesive composition is relatively rigid, particularly since the quantity of plasticizer is small. Arranging the bio-adhesive composition 3 in spaced-apart patterns 11 confers greater flexibility to the textile implant 1, in particular allowing it to be rolled up.

In operation, the textile implant 1 is preferably inserted using a trocar having a diameter of about 10 mm to 12 mm, with the rolled-up textile implant 1 placed therein, and it is subsequently pushed through the trocar into the implantation zone. The dry bio-adhesive composition 3 is sufficiently rigid to confer good shape memory to the textile implant 1, thereby enabling it to deploy easily and completely on leaving the trocar. The bio-adhesive composition 3 nevertheless retains relative flexibility enabling the textile implant 1 to fit closely to the zone 10 of the peritoneum 6 that is to be reinforced over the entire height of the first face 2a.

On coming into contact with the moist or even wet medium of the water-containing tissues, the adhesive function of the bio-adhesive composition 3 is activated, and the textile implant 1 immediately adheres to the zone 10. The quantity and the adhesive power of the bio-adhesive composition 3 are sufficient to enable the practitioner to reposition the textile implant 1 properly as often as desired, and for the textile implant 1 to remain in said initial implantation position on the zone 10 for reinforcement during at least 28 days, corresponding to the mean length of time needed for fibrosis to develop and hold the textile piece 2 definitively on said zone 10. In addition, the adhesive power and the quantity of the bio-adhesive composition are sufficient for the textile implant 1 not to collapse and for the entire surface of the face 2a to remain in contact with the zone 10 for reinforcement long enough for fibrosis and conjunctive tissue development to take place so as to fasten the textile piece 2 definitively. At the end of this period of about 28 days, the bio-adhesive composition 3 is completely absorbed and is eliminated naturally by the organism so that only the textile piece 2 of low weight per unit area, of the order of 30 g/m$^2$, remains and performs its role of mechanically reinforcing the zone 10.

Table 1 shows the results of a Good Laboratory Practice (GLP) study seeking to evaluate the results of implanting the textile implant 1 as shown in FIGS. 1 and 2 in an animal using laparoscopy. The animals tested were pigs. Reference markers, specifically clips, were placed at the four corners of the textile implant 1 after it had been implanted in order to identify after explanation whether the textile implant 1 had migrated.

TABLE 1

|  | 1st day | 7th day | 28th day |
| --- | --- | --- | --- |
| Number of pigs tested | Group I: 6 | Group II: 6 | Group III: 6 |
| Number of textile implants (1) tested | 11 | 12 | 12 |
| Results on implantation | 11 score++++ | 12 score++++ | 12 score++++ |
| Results on explantation | 3 score++++ 6 score+++ 2 score+ | 1 score++++ 8 score+++ 2 score++ 1 score+ | 3 score++++ 7 score+++ 2 score++ |

The legend for Table 1 is as follows:
++++: very good;
+++: good;
++: medium;
+: poor On the first day, when the textile implant 1 was implanted, evaluating migration took account of: the implant retaining proper positioning, ease of manipulation, and the immediate adhesive effect. At the time of explanation, evaluation took account of: any migration of the textile implant 1; retention in a deployed state; and the long-term adhesive effect. The technique used imitated hernia repair by laparoscopy. As it happens, no hernia reoccurred in the animals tested. Each period: 1st day, 7th day, 28th day, corresponds to a respective group of animals, Group I, Group II, and Group III. A poor result on implantation is characterized by positioning being difficult, adhesive power non-existent, poor deployment of the textile implant 1 on leaving the trocar, and migration away from its initial position. A good result on implantation is characterized by easy positioning, no migration of the textile implant 1 from its initial implantation position, strong adhesive power, and good deployment of the textile implant 1 on leaving the trocar. An implantation result described as "good" tends towards a result that is very good, and a "medium" result tends towards a passable result.

It should be observed that all of the implantation results were very good, which means that the textile implant 1 adheres immediately to the human tissue that is to be reinforced, is easily repositioned, and possesses strong adhesive power. During explanation of the textile implant 1, about 80% of the tested implants gave results that were very good or good, which means that they were still in place after 7 or 28 days of implantation, properly against the wall for reinforcement, without collapsing and above all without migrating from the initial position in which the practitioner had placed them. These results are thus most conclusive.

Figure 3:
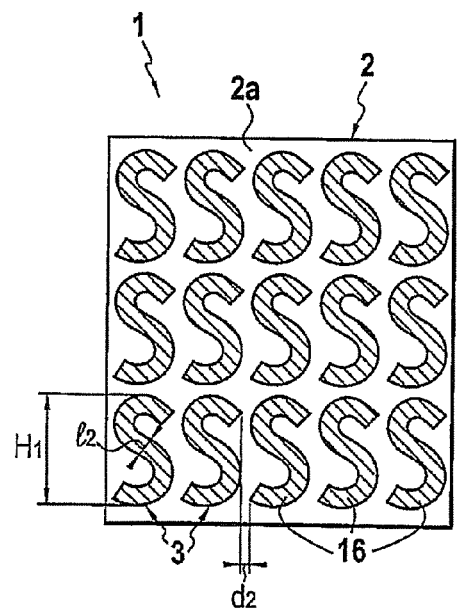
FIG. 3 is a diagrammatic representation of a second variant of the first face of a textile implant of the present invention.

FIG. 3 shows a variant of the patterns 11 supported by the first face 2a of the textile implant 1. The bio-adhesive composition 3 is covered in chiral patterns 16 on the first face 2a. The patterns 16 in question are S-shaped of width l2 of about 8 mm and about H1 of 20 mm and they are spaced apart by a distance d2 of about 1.5 mm. Given that the bio-adhesive compositions are transparent and that the textile piece 2 has openings, it is difficult for the practitioner in theater to distinguish between the first face 2a and the second face 2b. In the present example, the patterns 16 applied to the first face 2a are of a shape such that they appear differently depending on whether they are being observed from the first face 2a or by transparency from the second face 2b, thus making it possible for the practitioner to identify rapidly, and certainly, which face is the first face 2a carrying the activatable adhesive function.

Figure 4:
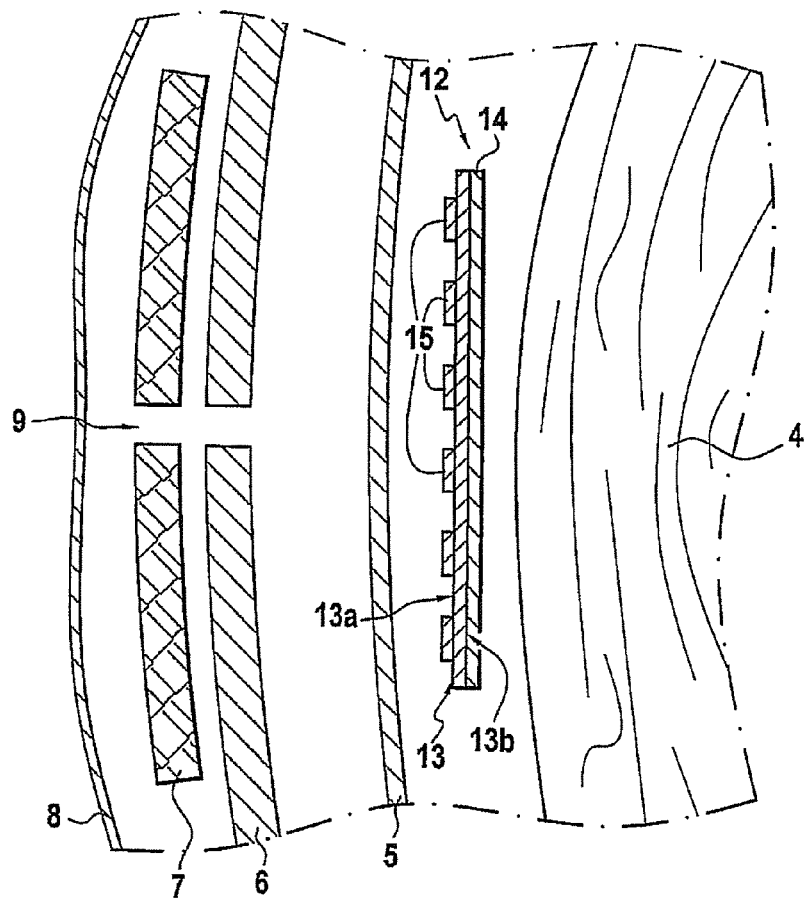
FIG. 4 is a diagrammatic representation in cross-section of a second example of a textile implant of the present invention shown in the organism for intra-abdominal intra-peritoneal hernia repair.

The textile implant 12 shown in FIG. 4 is for intra-abdominal intra-peritoneal hernia repair. It comprises a textile piece 13 having a first face 13a and a second face 13b completely covered in a polymer material 14 having a coefficient of friction of less than 0.1, and preferably a fluorinated polymer or a silicone based polymer. In this particular example, the polymer material 14 is in the form of an expanded polytetrafluoroethylene (ePTFE) film. The first face 13a is covered in a bio-adhesive composition 15 having the same formulation as the above-described bio-adhesive composition 3. The textile piece 13 is identical to the textile piece 2. The textile implant 12 in this example is placed in the organism between, on one side, the internal organs 4 and on the other side the peritoneum 5, the abdominal wall 6, a layer of adipose tissue 7, and the skin 8, in register with the eventration or hernia orifice 9 once the hernia has been pushed back (not shown). The textile piece 13 has a weight per unit area lying in the [15, 200] $g/m^2$, and preferably in the range [30, 100] $g/m^2$. As a specific example, the textile piece 13 has a weight per unit area of about 30 $g/m^2$. The bio-adhesive composition 15 has a weight per unit area lying in the range [5, 70] $g/m^2$, and preferably in the range [12, 50] $g/m^2$. The bio-adhesive composition 15 is applied in patterns (not shown) that are spaced apart by at least 1 mm, so the textile implant 12 retains its flexibility, and is suitable for being rolled up in order to be inserted in a trocar having a diameter of the order of 10 mm to 12 mm.

In operation, the principle, in particular the adhesive function, is the same as for the textile implant 1. Nevertheless it differs in that the Applicant has observed, surprisingly, that the quantity of bio-adhesive composition 15 needed to perform the same functions as those described above for the textile implant 1 is considerably reduced since the weight per unit area of the bio-adhesive composition 15 is equal to or slightly greater than at least one-third of the weight per unit area of the textile piece 13. A non-exhaustive explanation is that since the second face 13b is covered in a polymer material 14 having a very low coefficient of friction, the internal organisms 4 cannot catch on the textile implant 12, in particular by fibrosis, so that being located between the internal organs 4 and the peritoneum 5, the textile implant 12 is subjected to less mechanical stress than is the textile implant 1 between the abdominal wall 6 and the peritoneum 5.

The bio-adhesive composition 15 may be applied using particular patterns, optionally chiral patterns, providing they are spaced apart by at least 1 mm so that the bio-adhesive composition 15 is not spoilt, in particular does not crack when the textile implant 12 is rolled up. In this example, the practitioner has no difficulty in theater distinguishing between the first face 13a and the second face 13b because of the ePTFE film 14.

The bio-adhesive compositions 3 and 15 are prepared from a disposition of at least one bio-adhesive polymer, in particular PVP such as Kollidon 90F® by BASF®, with less than 4% plasticizer, preferably less than 2% plasticizer, and by way of specific example about 1% plasticizer, such as PEG, together with a sufficient quantity of distilled water. The proportions by weight are of the order of 70% distilled water, 30% of at least one hydrosoluble bio-adhesive polymer, and about 0.5% plasticizer. Thereafter, the bio-adhesive composition is applied to the first face of the textile piece by printing, in particular by means of a stencil or by means of etched rollers. Thereafter the textile implant is stoved so as to evaporate off the water. Once the textile implant has cooled down, it is placed in a packaging sachet and then sterilized, preferably with ethylene oxide. This known sterilization technique raises the temperature inside the packaging sachet to about 60° C. and kills the germs. Sterilization using gamma rays does not give satisfaction since the polypropylene is degraded and the bio-adhesive polymer runs the risk of curing with the plasticizer, which would then prevent it from dissolving away completely in the organism and being absorbed.

The invention claimed is:

1. A textile implant including a bio-adhesive composition to adhere the implant to a surgical site, in particular for repairing hernias, the implant comprising a textile piece having a first face completely or partially covered in the bio-adhesive composition that is hydrosoluble and absorbable, the bio-adhesive composition consisting essentially of a bio-adhesive polyvinylpyrrolidone (PVP) polymer that is hydrosoluble and absorbable, and a plasticizer that ranges only from about 1% to less than 4% by weight of said bio-adhesive composition such that the textile implant may be rolled up without the bio-adhesive composition cracking, with the adhesive function of the PVP polymer being activatable in a moist or wet medium.

2. A textile implant according to claim 1, wherein plasticizer ranges only from about 1% to less than 2% by weight of said composition.

3. A textile implant according to claim 1, wherein the plasticizer has a weight average molecular mass lying in the range 100 g/mol to 700 g/mol.

4. A textile implant according to claim 1, wherein, on the first face of the textile piece, the bio-adhesive composition is deposited in patterns that are spaced apart from one another by at least 1 mm.

5. A textile implant according to claim 4, wherein the patterns are parallel strips, having a width of about 4 mm and spaced apart by about 2 mm.

6. A textile implant according to claim 4, wherein the patterns are chiral, having an S-shape with a width of about 5 mm to 8 mm, a height of about 20 mm, and spaced apart by about 1.5 mm.

7. A textile implant according to claim 1, wherein the weight per unit area of the textile piece lies in the range of 15 to 200 $g/m^2$.

8. A textile implant according to claim 1, wherein the weight per unit area of said bio-adhesive composition is greater than or equal to three times the weight per unit area of the textile piece.

9. A textile implant according to claim 8, wherein the weight per unit area of the bio-adhesive composition lies in the range of 45 to 600 $g/m^2$.

10. A textile implant according to claim 1, wherein:
    a second face of the textile piece is completely or partially covered in a polymer material having a coefficient of friction of less than 0.1; and
    the weight per unit area of said bio-adhesive composition is at least equal to or greater than one-third of the weight per unit area of the textile piece.

11. A textile implant according to claim 10, wherein the second face is covered in a film of a fluorinated polymer material.

12. A textile implant according to claim 10, wherein the weight per unit area of the bioadhesive composition lies in the range of 5 to 70 g/m$^2$.

\* \* \* \* \*